US009833444B2

(12) United States Patent
Tambourgi et al.

(10) Patent No.: US 9,833,444 B2
(45) Date of Patent: Dec. 5, 2017

(54) **USE OF CHEMICAL COMPOUNDS THAT CAN INHIBIT THE TOXIC ACTIVITY OF SPHINGOMYELINASE D FROM VENOMS OF *LOXOSCELES* SPIDERS AND PHARMACEUTICAL COMPOSITION COMPRISING SAID COMPOUNDS**

(71) Applicant: FUNDAÇÃO BUTANTAN, São Paulo (BR)

(72) Inventors: Denise Vilarinho Tambourgi, São Paulo (BR); Priscila Hess Lopes, São Paulo (BR); Mario Tyago Murakami, São Paulo (BR); Fernanda Calheta Vieira Portaro, São Paulo (BR)

(73) Assignee: FUNDAÇÃO BUTANTAN, São Paulo (BR)

( * ) Notice: Subject to any disclaimer, the term of this patent is extended or adjusted under 35 U.S.C. 154(b) by 0 days.

(21) Appl. No.: 15/100,953

(22) PCT Filed: Dec. 2, 2014

(86) PCT No.: PCT/BR2014/050025

§ 371 (c)(1),
(2) Date: Aug. 1, 2016

(87) PCT Pub. No.: WO2015/081407

PCT Pub. Date: Jun. 11, 2015

(65) Prior Publication Data

US 2016/0367533 A1 Dec. 22, 2016

(30) Foreign Application Priority Data

Dec. 2, 2013 (BR) .......................... 1020130310433

(51) Int. Cl.
*A61K 31/443* (2006.01)
*A61K 31/404* (2006.01)

(52) U.S. Cl.
CPC .......... *A61K 31/443* (2013.01); *A61K 31/404* (2013.01)

(58) Field of Classification Search
CPC ............................ A61K 31/443; A61K 31/404
See application file for complete search history.

(56) References Cited

U.S. PATENT DOCUMENTS

2009/0163545 A1* 6/2009 Goldfarb .............. A61K 31/122 514/312
2010/0099881 A1 4/2010 Nishizawa et al.
2012/0232072 A1* 9/2012 Kumar ................ C07D 471/04 514/230.5

FOREIGN PATENT DOCUMENTS

WO 0174343 A2 10/2001
WO 2006097489 A1 9/2006
WO 2007104726 A1 9/2007
WO 2008022771 A1 2/2008

OTHER PUBLICATIONS

International Search Report for PCT/BR14/050025 dated Feb. 9, 2015, 4 pages.
Paixão-Cavlcante et al., "Tetracycline Protects against Dermonecrosis Induced by *Loxosceles* Spider Venom," Journal of Investigative Dermatology, 2007, vol. 127, pp. 1410-1418.

* cited by examiner

*Primary Examiner* — Yong Chu
(74) *Attorney, Agent, or Firm* — Banner & Witcoff, Ltd.

(57) ABSTRACT

The present invention relates preferably to the use of 4-bromo-N-[(E)-(2-methyl-1H-indol-3-yl)methyleneamino] benzenesulphonamide and 4-methyl-3-oxo-2-(3-pyridylmethylene) benzo[3,4-b]furan-6-yl-4-chlorobenzenesulphonate (compounds 5 and 6, respectively), which are compounds that can inhibit the toxic activity of sphingomyelinase D from *Loxosceles* venom, controlling the development of cutaneous and systemic loxoscelism; reducing haemolysis; inhibiting the formation of skin lesions; inhibiting skin necrosis; inhibiting intracellular signaling pathways and the production of reactive oxygen species. In addition to the therapeutic potential thereof, said inhibitors can be used to study the activity of sphingomyelinases and phospholipases D. The present invention also relates to a pharmaceutical composition for treating loxoscelism, reducing haemolysis, inhibiting the formation of skin lesions, inhibiting skin necrosis, inhibiting intracellular signaling pathways and the production of reactive oxygen species, comprising said compounds and a pharmaceutically acceptable carrier.

12 Claims, 10 Drawing Sheets

Dose-response curves and $IC_{50}$ of compounds

USE OF CHEMICAL COMPOUNDS THAT CAN INHIBIT THE TOXIC ACTIVITY OF SPHINGOMYELINASE D FROM VENOMS OF *LOXOSCELES* SPIDERS AND PHARMACEUTICAL COMPOSITION COMPRISING SAID COMPOUNDS

FIELD OF THE INVENTION

The present invention relates to the use of chemical compounds capable of inhibiting the toxicity of sphingomyelinase D of the venom of spider *Loxosceles.* More specifically, the instant invention relates to the use of benzenesulfonamides and benzenesuphonates on toxicity inhibition of sphingomyelinase D of the venom of spider *Loxosceles.*

BACKGROUND OF THE INVENTION

Loxoscelism (accident involving brown recluse spider) has been described in several continents. It corresponds to the most severe form of araneism in Brazil. The majority of accidents notified occur in the South Region of the country, particularly in Paraná and Santa Catarina. The accident occurs more commonly with adults, with a small predominance in women, occurring at home. A centripetal distribution of insect bites is observed, which affect more the thigh, the upper body or arm.

The most important component of *Loxosceles* venom is sphingomyelinase D, that acts on the extracellular matrix and through the activation of the complement system and action on endothelial cells, epithelial cells, leukocytes and platelets, which causes the release of inflammatory mediators, obstruction of small vessels at the site of venom inoculation and consequent tissue damage. Likewise, hemolysis has been attributed to the action of sphingomyelinase-D on endogenous metalloproteinases. Once activated, they act on the membrane proteins of red blood cells, making them susceptible to complement action.

The Brazilian patent application PI 0514809-0 A, filed on Aug. 29, 2005, on behalf of National Autonomous University of Mexico) and Laboratorios Silanes S.A. of C.V. and entitled: "Imunógeno e antiveneno contra o veneno da aranha marrom" describes the isolation, characterization and expression of coding DNA fragments of sphingomyelinases D of 3 species of spiders of the genus *Loxosceles: L. boneti, L. reclusa* and *L. laeta* and its use as an immunogen for the production of neutralizing antibodies of the corresponding venom and of respective F(ab')2 fragments. Said document PI 0514809-0 also reports the use of recombinant sphingomyelinases D as part of an antigenic array useful in immunopurifying antibodies and its fragments as part of a diagnostic device for venoming by spider of the genus *Loxosceles.*

As can be observed, document PI 0514809-0 basically describes the production of recombinant sphingomyelinases for producing neutralizing antibodies against spider venom of the genus *Loxosceles* and its use in compositions for treating venoming by these spiders. In no time document PI 0514809-0 describes or suggests the use of inhibitor compounds belonging to the class of benzenesulfonamides and chloro-benzenesulfonates for treating symptoms associated with loxoscelism caused by the bite of spiders belonging to genus *Loxosceles.*

The international patent application WO 01/74343, filed on Mar. 30, 2001, published on Oct. 11, 2001; on behalf of 3M INNOVATIVE PROPERTIES COMPANY and entitled: "Method for the treatment of dermal lesions caused by envenomation" relates to a method of treating skin lesions caused by venoming, comprising the application, at the site of injury, of a therapeutically effective amount of a modifier compound of the immune response selected from the group consisting of imidazoquinoline amines, imidazopyridine amines, 6.7-fused cycloalkyl imidazopyridine amines, imidazonaphtiridine amines, tetra-hydro imidazonaphtiridine amines, oxazolopyridine amines, oxazoloquinoline amines, thiazolopyrimidine amines, thiazoloquinoline amines and 1.2-bridged imidazoquinoline amines.

As noted, the international patent application WO 01/74343 only provides the use of known immune response modifier (IRMs) compounds mentioned above, which are able to stimulate the innate and acquired immune response for the treatment of skin lesions by venoming caused, for example, by bites of spiders of the genus *Loxosceles,* among others. Said international patent application WO 01/74343 neither mentions nor suggests the use of specific inhibitor compounds to sphingomyelinases (D) present in the venom of spiders of the genus *Loxosceles* for the treatment of skin lesions and/or to avoid developing loxoscelism.

The international patent application WO 2007/149343, filed on Jun. 15, 2007, published on Dec. 27, 2007; on behalf of THE BOARD OF TRUSTEES OF THE LELAND STANFORD JUNIOR UNIVERSITY and entitled: "Proteases for treatment of venemous bites" relates to materials and methods, including kits, for use in the treatment of snake bites, bee stings, spider bites and other forms of venoming or exposure to toxins. The materials and methods involve the use of proteases associated with the protective mechanism of mast cell degranulation, associated with a reduction in the toxic effects and increased survival rate in animal models. The proteases used are selected from the group containing chymases (specificity to a substrate similar to chymotrypsin), carboxypeptidase A, carboxypeptidase B, tryptases (specificity to a substrate similar to trypsin), chymotrypsin or papain.

Although the international patent application WO 2007/149343 uses, in its embodiment examples, treatment for venoming caused by spider *Loxosceles reclusa,* said international patent application WO 2007/149343 does not provide for the use of a specific inhibitor compound for sphingomyelinase D of spiders of the genus *Loxosceles.*

The international patent application WO 2008/022771, filed on Aug. 21, 2007, and published on Feb. 28, 2008; on behalf of NOVARTIS A G and entitled: "Amides as sphingomieline inhibitors" describes a formulation that provides the use of acid sphingomyelinase for treating disorders mediated by the activity of acid sphingomyelinase present in the lysosome of mammalian cells, such as autoimmune diseases, diseases involving abnormal apoptosis and tumor growth. Therefore, said document does not describe any compounds that can specifically inhibit the toxicity of sphingomyelinases D from the venoms of spiders of the genus *Loxosceles,* controlling the development of cutaneous and systemic loxoscelism.

The U.S. patent application US 2010/0099881 A1 (which corresponds to the international application PCT/JP2008/053936), filed on Dec. 7, 2009, and published on Apr. 22, 2010; on behalf of Mugio Nishizawa, Hiroshi Imagawa, Jun Sakurai, Masataka Oda and Otsuka Chemical Co. LTD. and entitled: "Sphingosine compound, method for producing the same, and sphingomyelinase inhibitor", only discloses a new sphingosine compound, with inhibitory activity of sphingomyelinase suitable for use as a medicine for treating or preventing cerebral hemorrhage, cerebral infarction and similar cerebrovascular diseases, head injuries, senile dementia, Alzheimer's and Parkinson's disease, among other similar degenerative diseases, diabetes, obesity, atherosclerosis, inflammatory diseases, autoimmune diseases, cancer, kidney disease and heart diseases.

The article published in *Journal of Investigative Dermatology* (2007), volume 127, pages 1410 to 1418, available online on Jan. 11, 2007, Authors: Danielle Paixão-Cavalcante, Carmem W. van der Berg, Rute M. Gonçalves-de-Andrade, Matheus de F. Fernandes-Pedrosa, Cinthya Kimori Okamoto e Denise V. Tambourgi, entitled: "*Tetracicline protects against dermonecrosis induced by loxosceles spider venom*", relates to the use of classic tetracycline antibiotics (tetracycline, doxycycline and minocycline) in the inhibition or reduction of dermonecrotic lesions and to the mechanisms involved in the development of cutaneous loxoscelism induced by the venom of *Loxosceles* spiders through in vitro and in vivo experiments. According to this document, the topical treatment is more effective in the prevention or reduction of dermonecrotic lesions than the oral (systemic) treatment, possibly by the concentration of tetracyclines used which, in high systemic concentrations, can lead to toxicity. According to said document, the binding of sphingomyelinase D from the venom of *Loxosceles* spiders to the cell surface induces the expression and activation of endogenous metalloproteinases (MMPs). Thus, the mechanism of action proposed in the document involves the tetracycline inhibitory action on metalloproteinases (MMPs), whose expression and activation are induced by the venom of *Loxosceles* spiders. In no time said document refers to the use of compounds belonging to the class of benzenesulfonamides and chloro-benzenesulfonates with similar purposes.

As can be observed, there is no state of the art document that describes or suggests the use of inhibitor compounds belonging to the class of benzenesulfonamides and benzenesulfonates for treating symptoms associated with loxoscelism caused by the bite of spiders belonging to genus *Loxosceles.*

Dictionary—See detailed dictionary

SUMMARY OF THE INVENTION

In order to solve the problems mentioned above, this invention provides significant advantages related to the use of inhibitor compounds belonging to the class of benzenesulfonamides and benzenesulphonate for treating symptoms associated with loxoscelism caused by the bite of spiders belonging to genus *Loxosceles,* enabling an increase in their performance and offering a more favorable cost/benefit ratio.

This invention relates to the use of inhibitors compounds belonging to the class of benzenesulfonamides and benzenesulphonate with inhibitory activity on sphingomyelinases D of the venom of *Loxosceles* spiders for preparing a medicine to act on the hydrolytic activity of recombinant sphingomyelinase D toxin (SMase D) and of the venom of brown recluse spider *Loxosceles laeta.*

The present invention preferably relates to the use of 4-bromo-N-[(E)-(2-methyl-1H-indol-3-yl) methyleneamino]benzenosulfonamide and of 4-methyl-3-oxo-2-(3-pyridylmethylene)benzo[3,4-b]furan-6-yl-4-chlorobenzenesulfonate (compounds 5 and 6, respectively), which are compounds that can inhibit the toxicity action of sphingomyelinases D of the venom of *Loxosceles,* controlling the development of cutaneous and systemic loxoscelism; reduction of hemolysis, inhibition of cutaneous lesion, inhibition of dermonecrosis, inhibition of the intracellular signaling pathways and production of reactive oxygen species. Besides of the therapeutic potential, such inhibitors can be used as tools in the study of the action of sphingomyelinases and phospholipases D.

In a second aspect, this invention relates to a pharmaceutical composition for treating loxoscelism, hemolysis reduction, inhibition of cutaneous lesion, inhibition of dermonecrosis, inhibition of intracellular signaling pathways and production of reactive oxygen species, which comprises a benzenesulfonamide compound and a pharmaceutically acceptable vehicle. The benzenesulfonamide compound preferably being the compound 4-bromo-N-[(E)-(2-methyl-1H-indol-3-yl)methyleneamine]benzenesulfonamide.

A third aspect of this invention relates to a pharmaceutical composition for treating loxoscelism, hemolysis reduction, inhibition of cutaneous lesion, inhibition of dermonecrosis, inhibition of intracellular signaling pathways and production of reactive oxygen species, which comprises a benzenesulphonate compound and a pharmaceutically acceptable vehicle. The benzenesulphonate compound preferably being compound 4-methyl-3-oxo-2-(3-pyridylmethylene)benzo[3,4-b]furan-6-yl-4-chlorobenzenesulfonate.

BRIEF DESCRIPTION OF THE DRAWINGS

The structure and operation of the invention, along with the additional advantages thereof, can be better understood by reference to the attached drawings and the description that follows.

Figure 1:
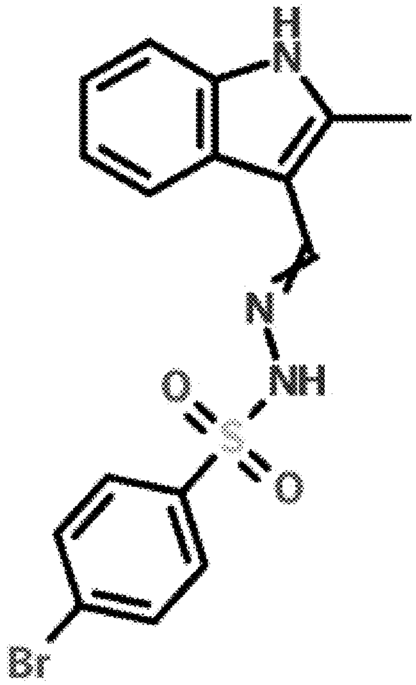
FIG. 1 shows the structural formula of compound 5-4-bromo-N-[(E)-(2-methyl-1H-indol-3-yl) methyleneamino] benzenosulfonamide.

Annex 1 shows microphotographs of histopathological analysis of the skin of rabbits inoculated with the venom of *L. laeta* or with the venom incubated with compounds 5 and 6.

DETAILED DESCRIPTION OF THE INVENTION

Although this invention can be susceptible to different embodiments, a preferred embodiment is shown in the drawings and in the following detailed discussion, with the understanding that this embodiment should be considered an example of the principles of the invention without the intention of limiting the present invention to what has been illustrated and described herein.

This invention relates to the use of inhibitors compounds belonging to the class of benzenesulfonamides and benzenesulphonate with inhibitory activity on sphingomyelinases D of the venom of *Loxosceles* spiders for preparing a medicine to act on the hydrolytic activity of recombinant sphingomyelinase D toxin (SMase D) and of the venom of brown recluse spider *Loxosceles laeta.*

Figure 2:
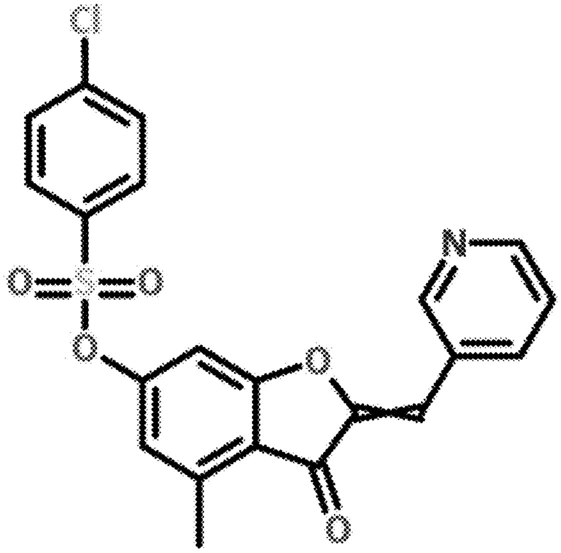
FIG. 2 shows the structural formula of compound 6-4-methyl-3-oxo-2-(3-pyridylmethylene)benzo[3,4-b]furan-6-yl-4-chlorobenzenesulfonate.

The present invention preferably relates to the use of 4-bromo-N-[(E)-(2-methyl-1H-indol-3-yl) methyleneamino]benzenosulfonamide, named compound 5 (FIG. 1) and of 4-methyl-3-oxo-2-(3-pyridylmethylene) benzo[3,4-b]furan-6-yl-4-chlorobenzenesulfonate, and compound 6 (FIG. 2), which are compounds that can inhibit the toxicity of sphingomyelinases D of the venom of *Loxosceles,* controlling the development of cutaneous and systemic loxoscelism, treatment of loxoscelism, reduction of hemolysis, inhibition of cutaneous lesion, inhibition of dermonecrosis, inhibition of the intracellular signaling pathways and production of reactive oxygen species. Besides of the therapeutic potential, such inhibitors can be used as tools in the study of the action of sphingomyelinases and phospholipases D.

The inhibitor compounds of the present invention can be used as tools in the study of the action of sphingomyelinases and phospholipases D, and these inhibitors have therapeutic potential to venoming by *Loxosceles* spiders and infections by SMases producer microorganisms.

Selection of Compounds

The binders used in molecular Docking studies were selected from a free database of commercially available molecules, the ZINC Database (www.zinc.docking.org). Many ligands in this database are available in a variety of 3D formats immediately usable by many popular docking programs.

In addition to the important physical-chemical properties, the bank contains supplier information and numbers of the original catalogue for each commercial source of this compound. It is also possible to find information about the function or activities already studied for the compound, when available.

Molecular Docking Studies

Molecular docking studies for selecting SMases D inhibitors were conducted at the Laboratório Nacional de Luz Síncroton, Campinas—Sao Paulo, with the aid of ICM software—Molsoft (based on Monte Carlo algorithm) Molegro Virtual Docker, (based on a heuristic search algorithm that combines differential evolution with a cavity prediction algorithm) and GOLD (based on a genetic algorithm). The docking analysis were carried out based on the 3D structure of SMase I of the venom of *L. laeta,* according to article of MURAKAMI, M. T.; FERNANDES-PEDROSA, M. F.; TAMBOURGI, D. V.; ARNI, R. K. and entitled "*Structural basis for metal ion coordination and the catalytic mechanism of sphingomyelinases D*", published in the J. Biol. Chem., v. 280, No. 14, page 13658-13664, 2005, and incorporated herein by reference.

The following topics describe the action of compounds 4-bromo-N-[(E)-(2-methyl-1H-indol-3-yl)methyleneamino] benzenosulfonamide (FIG. 1) and 4-methyl-3-oxo-2-(3-pyridylmethylene)benzo[3,4-b]furan-6-yl-4-chlorobenzenesulphonate (FIG. 2), named as compounds 5 and 6 of this invention, in the mechanisms that underlie the development of cutaneous and systemic loxoscelism.

Analysis of the Inhibitory Action of Compounds 5 and 6 on the Hydrolytic Activity of the Toxin and Venom.

Compounds 5 and 6 of this invention were diluted in dimethyl sulfoxide (DMSO) and prepared in a stock solution of high concentration, which was diluted in sterile saline solution to the concentrations used in each assay.

In the fluorimetric assays, the basal fluorescence of the compounds was measured and deducted from these assays.

The ability of the compounds in the concentration of 40 μM of inhibiting the hydrolytic activity of the recombinant toxin sphingomyelinase D (SMase D) and of the venom of *Loxosceles laeta* on substrates sphingomyelin (SM) and lysophosphatidylcholine (LPC), by fluorimetry assays, was analyzed.

Figure 3:
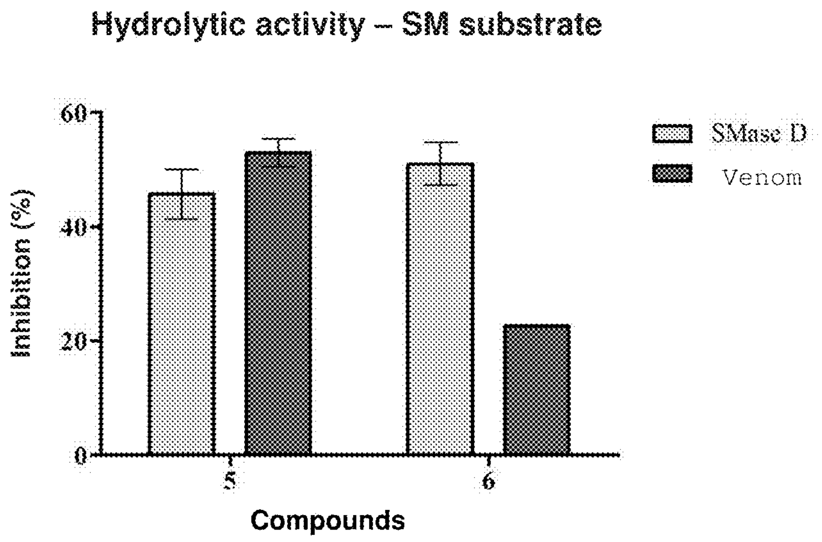
FIG. 3 shows a graphic indicating the inhibition ability of the hydrolytic activity of recombinant sphingomyelinases and present in the venom of *Loxosceles laeta,* on the substrate sphingomyelin (SM), by compounds 5 and 6.

FIG. 3 shows the inhibition percentage of compounds 5 and 6 on the hydrolytic activity of recombinant SMases D and present in the venom of *L. laeta,* on the sphingomyelin (SM) substrate.

The results showed that compound 5 of the present invention inhibits 45.7% and 53% of the activity of recombinant toxin and the venom of *L. laeta,* respectively, on the SM substrate. Compound 6 of the present invention inhibited 51% and 22.7% of the activity of the recombinant toxicity and the venom, respectively.

Figure 4:
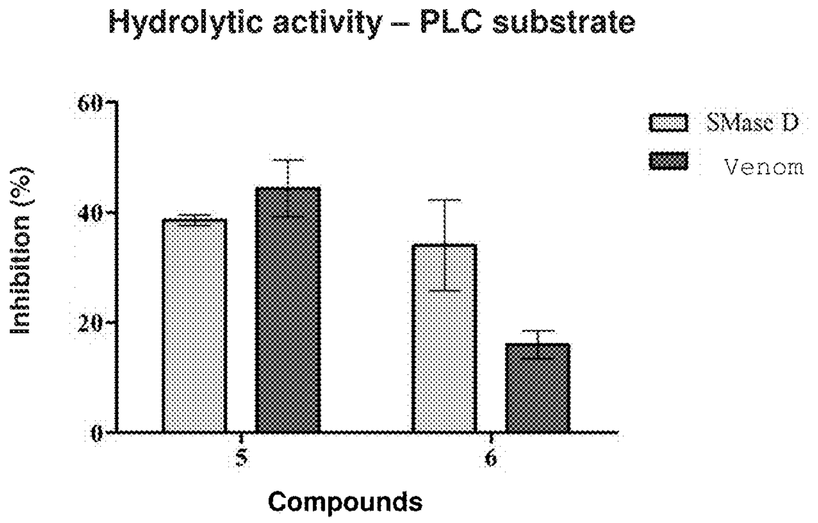
FIG. 4 shows a graphic indicating the inhibition ability of the hydrolytic activity of recombinant sphingomyelinases and present in the venom of *Loxosceles laeta,* on the substrate lysophosphatidylcholine (LPC), by compounds 5 and 6.

FIG. 4 shows the inhibition percentage of compounds 5 and 6 on the hydrolytic activity of recombinant SMases D and present in the venom of *L. laeta,* on the lysophosphatidylcholine substrate (LPC).

In relation to substrate LPC, compound 5 of the present invention reduces 38.6% and 44.4% of the activity of the recombinant toxin and the venom, respectively. As to compound 6 of this invention, it reduces 34 and 16% of this activity.

Figure 5:
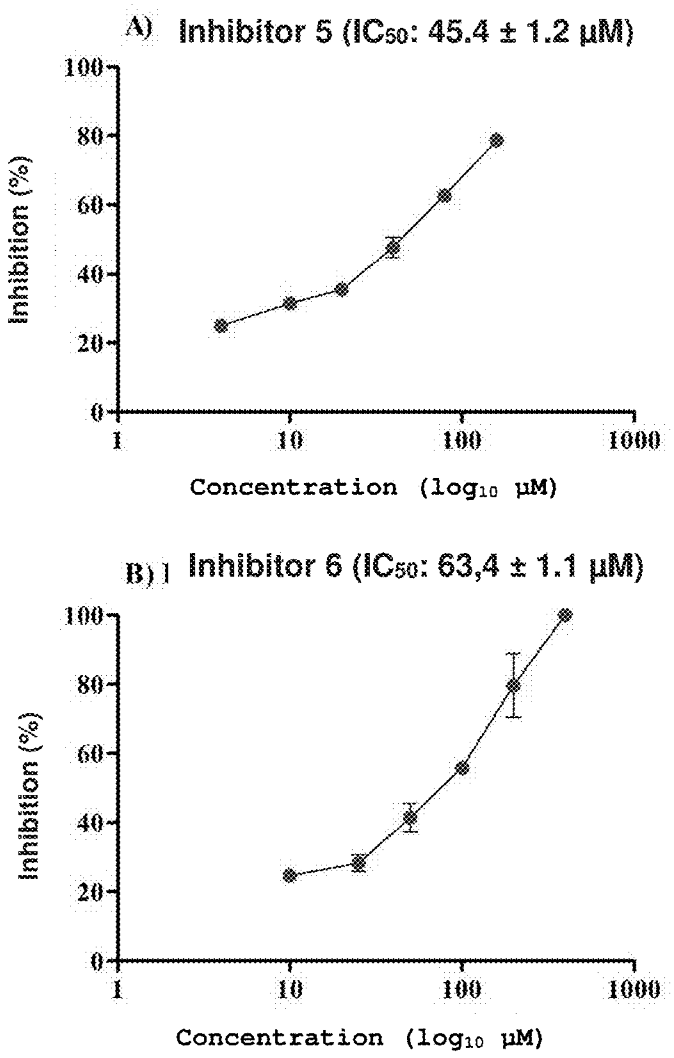
FIGS. 5 (*a*) and 5 (*b*) show the dose-response curves of compounds 5 and 6 in the inhibition of the hydrolytic activity on SM, on which basis the $IC_{50}$ values of compounds have been calculated.

FIGS. 5(*a*) and 5(*b*) show the dose-response curves of the inhibition of the hydrolytic activity of recombinant SMases D on the substrates sphingomyelin, respectively by compounds 5 and 6. Based on these curves, $IC_{50}$ of the compounds were calculated.

Based on said dose-response curves of the action of the compounds on the activity of the recombinant toxin on the substrate SM, the $IC_{50}$ values were obtained, which were 45.4±1.2 μM to compound 5 of this invention and 63.4±1.1 μM to compound 6 of this invention.

The analysis of the inhibition mechanism showed that compounds 5 and 6 of the present invention may be classified as uncompetitive action inhibitors with $K_i$ values of 1.63 and 1.73, respectively.

Analysis of the Action of Compounds 5 and 6 of the Present Invention on Hemolysis Induced by the Venom of *Loxosceles*

The removal of glycophorins from the surface of red blood cells by indirect action of the toxin is a crucial event for the development of intravascular hemolysis that occurs in accidents.

Figure 6:
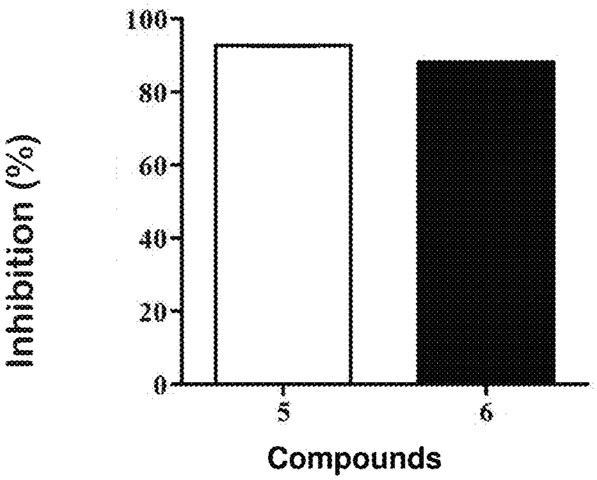
FIG. 6 presents the inhibition percentage of removal of glycophorin C from the surface of red blood cells by compounds 5 and 6, a crucial event in the development of complement system-dependent hemolysis observed in venoming.

FIG. 6 shows the inhibition percentage of the removal of glycophorins C of the surface of human red blood cells induced by SMases D present in the venom of *L. laeta.*

The analysis of the expression of glycophorin C on the surface of human red blood cells by flow cytometry showed that, in the presence of compounds 5 and 6 of the present invention (40 μM), the removal of these molecules from the surface of cells is reduced by 92.6 and 88.2%, respectively.

Figure 7:
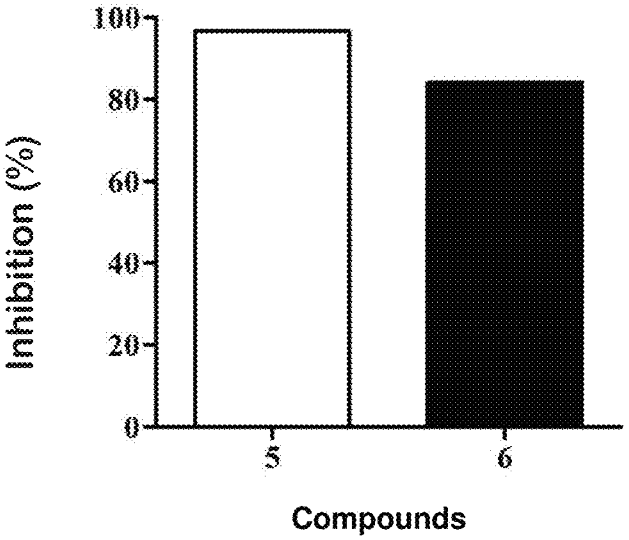
FIG. 7 shows the inhibition percentage of the sphingomyelinases D binding to the surface of red blood cells, by compounds 5 and 6.

FIG. 7 shows a graph indicating the inhibition percentage of the binding of SMases D present in the venom of *L. laeta* to the surface of human red blood cells.

This event of glycophorin C removal is associated to the binding of the toxin on the red blood cell membrane. Thus, the binding of the toxin to the cell surface was analyzed by flow cytometry and the results indicated a reduction of 96.8 and 84% in the presence of the compounds 5 and 6 of the present invention, respectively.

Analysis of the Action of Compounds 5 and 6 of the Present Invention on the Mechanisms of Cutaneous Loxoscelism The development of cutaneous lesion observed in the loxoscelism is closely related to the cell death of keratinocytes induced by SMase D.

Figure 8:
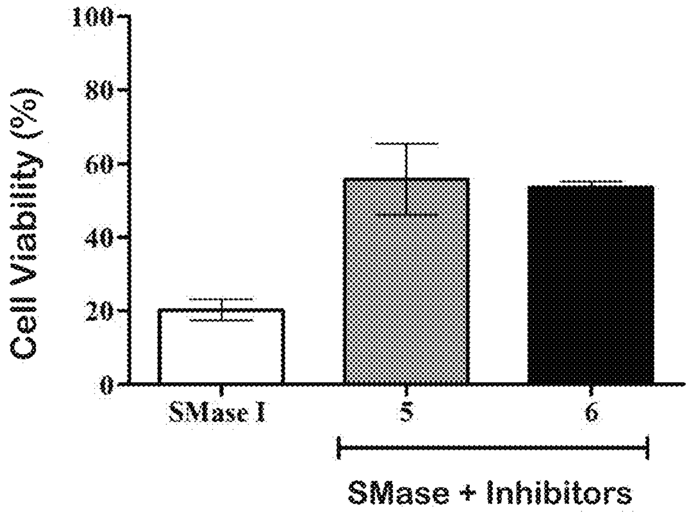
FIGS. 8 and 9 represent the ability of compounds 5 and 6 to reduce the death of human keratinocytes induced by recombinant sphingomyelinases present in the venom of *L. laeta;*

FIG. 8 shows the viability of human keratinocytes treated only with recombinant SMase D or incubated with the compounds 5 and 6. The analysis of cell viability by MTT method in vitro, after treatment with recombinant toxin or venom, showed that in the presence of the compound 5 of the present invention the viability of cells treated with the toxin increases in 20.23 to 55.75% and in the presence of the compound 6 of the present invention increases to 53.55%.

Figure 9:
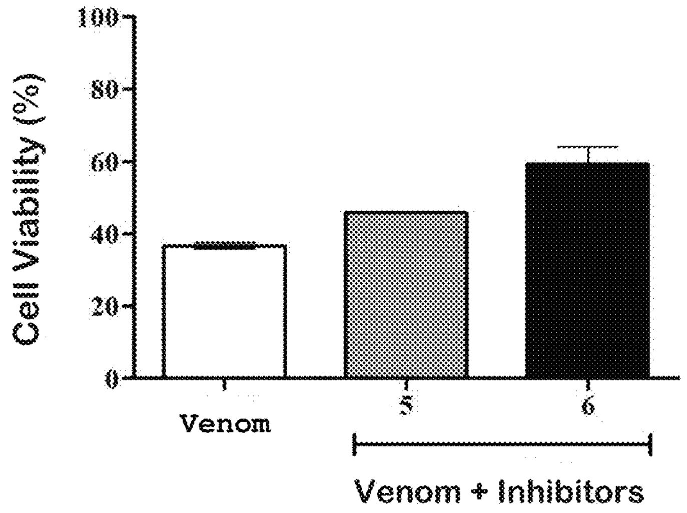

FIG. 9 shows the viability of human keratinocytes treated only with venom of *L. laeta* or with the venom incubated with compounds 5 and 6. The cells treated with venom had increased viability of 36.7 to 45.9%, with 5 of the present invention, and 59.26% with compound 6 of the present invention. For these assays, compounds 5 and 6 of this invention were used at a concentration of 10 μM.

As well as in erythrocytes, keratinocyte cell death is associated with the binding of the toxin to this cell membrane.

Figure 10:
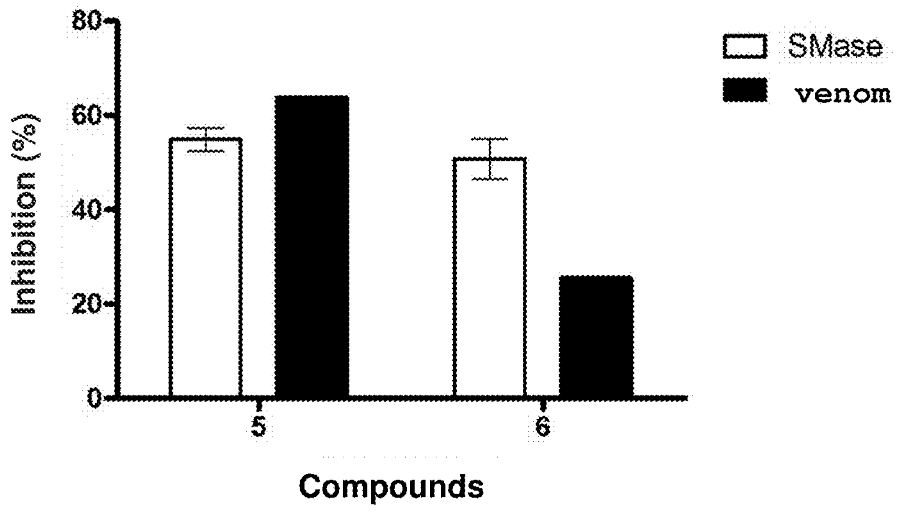
FIG. 10 shows the inhibition percentage of the binding of recombinant sphingomyelinases present in the venom to the cell membrane of human keratinocytes, by compounds 5 and 6.

FIG. 10 shows a graph indicating the inhibition percentage of the bonding of recombinant SMases D and present in the venom of *L. laeta* to the surface of human keratinocytes. The analysis of this parameter by flow cytometry showed that the binding of recombinant toxin is reduced by 54.9% with compound 5 of this invention and 50.77% with compound 6 of this invention, both at a concentration of 40 μM. The binding of SMases present in venom is reduced by 63.8 and 25.6% in the presence of compounds 5 and 6, respectively.

Other event associated with keratinocyte death during the development of skin lesion is the production of extracellular matrix metalloproteinases 2 and 9 (MMPs). Thus, the culture supernatant of keratinocytes treated with the venom of *L. laeta* was investigated by ELISA as for the presence of MMP-2 and 9. In the presence of compounds 5 and 6 of the present invention (10 μM), the MMP-2 secretion is reduced by 81 and 98.4%, respectively. In relation to MMP-9, both compounds completely inhibit the secretion of this MMP.

Figure 11:
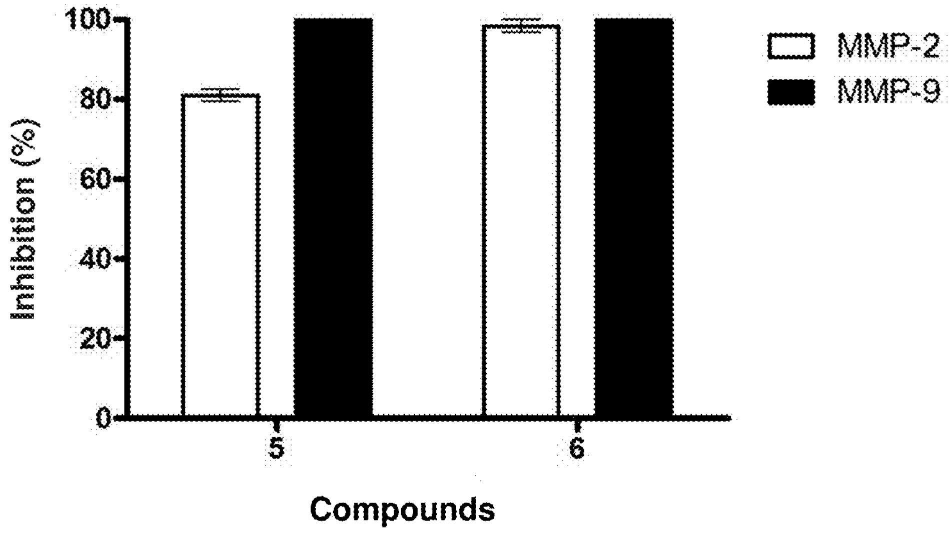
FIG. 11 describes the inhibition percentage of production/secretion of matrix metalloproteinases (MMP-2 and 9) by human keratinocytes treated with recombinant sphingomyelinases D promoted by compounds 5 and 6.

FIG. 11 shows a graph indicating the inhibition percentage of production/secretion of MMP-2 and 9 by human keratinocytes treated with the venom of *L. laeta.*

After analyzing the aspects involving the development of skin lesion, the ability of the compounds in inhibiting dermonecrosis in vivo was verified, using a model in rabbits.

After 24 hours of venom inoculation, the injury was reduced by 61.8 and 36% in the presence of compounds 5 and 6 of the present invention, respectively. In 48 hours, the inhibition was 60 and 45%, and in 72 hours, it was 56 and 49% in the presence of these two compounds.

Figure 12:
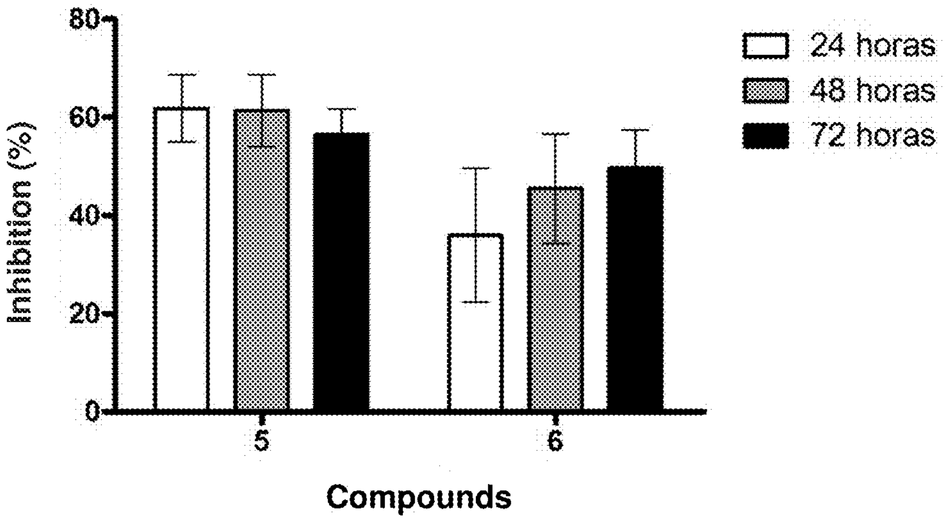
FIG. 12 shows the inhibition percentage of the development of dermonecrotic lesions in rabbits, analyzed 24, 48 and 72 hours after inoculation of the venom, by compounds 5 and 6.

FIG. 12 shows a graph indicating the inhibition percentage of dermonecrotic lesions developed in rabbits by inoculation of the venom of *L. laeta.*

The histopathological analysis of the skin of rabbits inoculated with the venom in the presence or absence of these compounds demonstrates that, in the presence of compounds 5 and 6 of the present invention, there is a reduction in the disorganization of the collagen fibers in the dermis, absence of hemorrhage and inflammatory infiltrate, as well as injury to the adjacent muscle layer in relation to that inoculated only with venom.

Annex 1 shows microphotographs of the histopathological analysis of the skin of rabbits inoculated only with the venom of *L. laeta* or with the venom incubated with compounds 5 and 6.

Compounds 5 and 6 of this invention were used at a concentration corresponding to three times the value of $IC_{50}$ (136.2 μM to compound 5 and 190.2 μM to compound 6).

Action of Compounds 5 and 6 of the Present Invention on Other Mechanisms Involved in the Toxicity of Sphingomyelinases D of the Venom of *Loxosceles*

Figure 13:
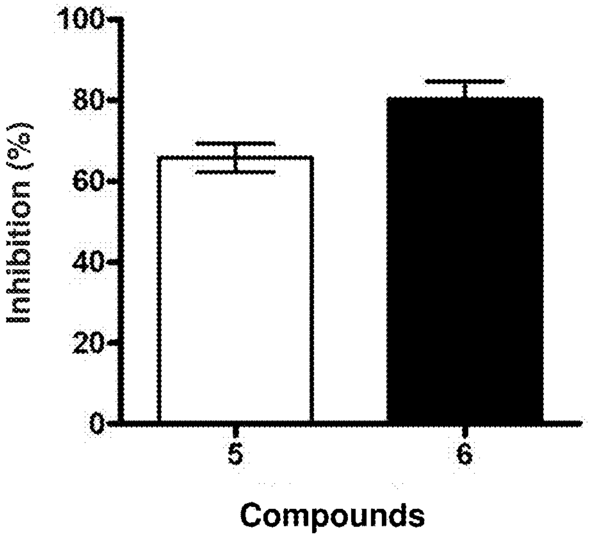
FIG. 13 represents the inhibition percentage of MAPK ERK1/2 intracellular signaling pathway activation in human keratinocytes treated with recombinant sphingomyelinases D by compounds 5 and 6.

FIG. 13 shows the percentage of inhibition of the activation of MAPK ERK1/2 intracellular signaling pathway induced by recombinant SMases D. The toxin was able to induce the intracellular MAPKs intracellular signaling pathway, more specifically, the ERK1/2 in keratinocytes. It was verified, in ELISA assays, that in the presence of compounds 5 and 6 of this invention (40 μM) the phosphorylated ERK1/2 was reduced by 65.8 and 80.2%, respectively.

Another aspect analyzed was the production of reactive oxygen species by keratinocytes treated with the toxin, using the flow cytometry technique.

Figure 14:
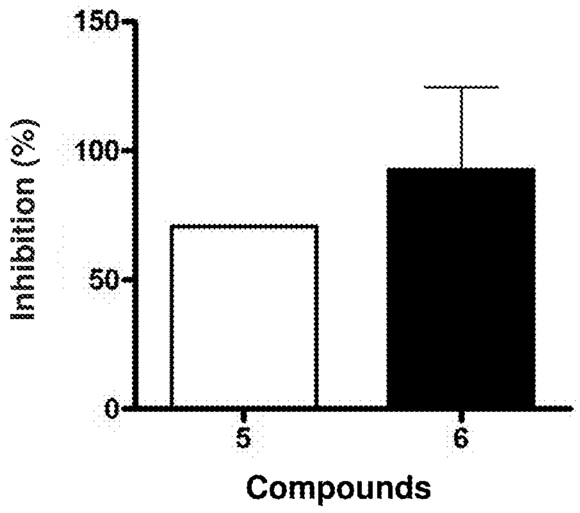
FIG. 14 shows the inhibition percentage of superoxide ion production by human keratinocytes treated with sphingomyelinases D recombinant, by compounds 5 and 6.

FIG. 14 shows the inhibition percentage of the production of superoxide ion by keratinocytes treated with recombinant SMases D.

The results indicate that, in the presence of compounds 5 and 6 of the present invention (40 µM), superoxide production by these cells was inhibited by 70.7 and 92.7%, respectively.

Additionally, the expression of the TNF receptor on the surface of keratinocytes treated with the toxin was analyzed by flow cytometry. The treatment with the toxin leads to a removal of the cell surface receptor, which is reversed by 27.7% in the presence of compound 5 of this invention (40 µM).

The production of cytokines by keratinocytes can be an important aspect in the development of skin lesion of loxoscelism.

Figure 15:
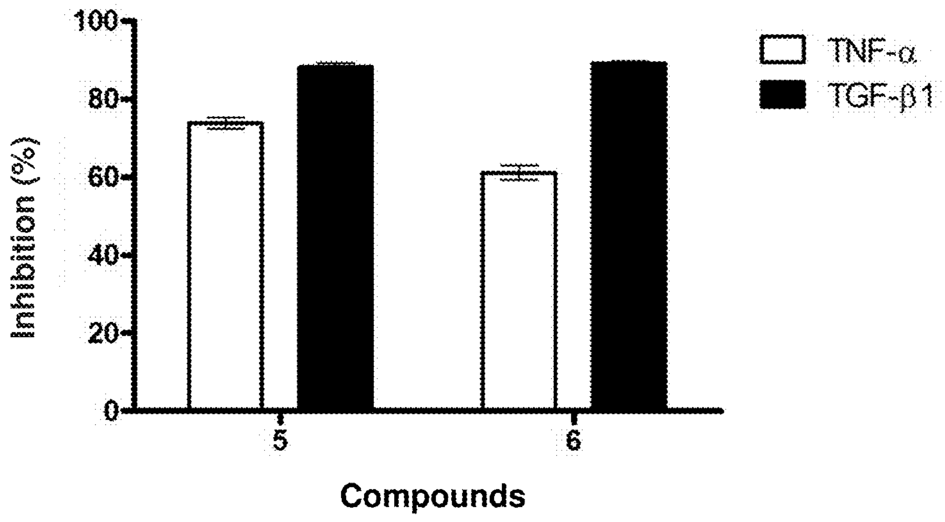
FIG. 15 shows the inhibition percentage of the production of cytokines TNF-α and TGF-β1 by human keratinocytes treated with the recombinant sphingomyelinases D, by compounds 5 and 6.

FIG. 15 shows the inhibition percentage of the production of cytokines by human keratinocytes treated with the recombinant SMases D. It was demonstrated, by ELISA, on the culture supernatant of keratinocytes treated with the toxin, that the same induces the production of TNF-α, which was reduced by 73.9 and 61.1% in the presence of compounds 5 and 6 (10 µM), respectively. Another cytokine found was TGF-β1, which was reduced by 88.3 and 89.2% in the presence of the compounds.

Figure 16:
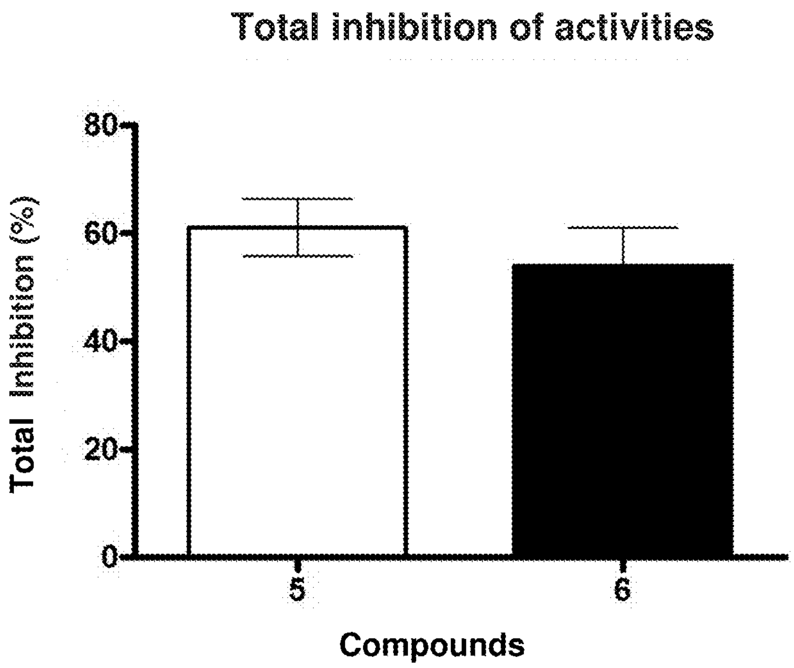
FIG. 16 shows the average inhibition of all activities tested for compounds 5 and 6.

FIG. 16 shows a graphic indicating the efficiency of compounds 5 and 6 in the inhibition of the mechanisms involved in the toxicity of SMases D and in the development of cutaneous and systemic loxoscelism.

Thus, taking into consideration all the aspects analyzed, compound 5 of the present invention is 61.1% efficient, while compound 6 of this invention is 54.1% efficient in relation to the mechanisms involved in the toxicity of SMases D in the development of loxoscelism.

Action of Inhibitor Compounds 5 and 6 on the Hydrolytic Activity on Substrate Sphingomyelin, of Bacterial Sphingomyelinases.

Phospholipases are important toxic components present in the venom of animals and bacterial toxins. They promote the hydrolysis of ester bonds of phospholipids, and they are classified in phospholipases A1, A2, C and D, by the position of hydrolyzed ester bond (VAN DEN BOSCH, 1980).

Contrary to other phospholipases, those found in the venom of *Loxosceles* (SMases D) and in certain bacteria have an unusual substrate specificity, since of the four major phospholipids present in mammal cell membranes, only sphingomyelin is hydrolyzed by bacterial LDP, while those of the venom of *Loxosceles* spiders cleave sphingomyelin, generating ceramide-1-phosphate as the hydrolysis product and are also able to hydrolyze lysophosphatidylcholine, generating lysophosphatidic acid (Bernheimer; Campbell; Forrester, 1985; Tambourgi et al., 1998; Van Meeteren et al., 2004). Researches on sequence databases showed that the toxins of the bacteria *Corynebacterium pseudotuberculosis* and *Arcanobacterium haemolyticum* are also sphingomyelinases and have between 24 and 34% of similarity with the first 30 amino acids of the *Loxosceles* toxins (Tambourgi et al., 1998), as well as similar molecular weight and isoelectric point (Bernheimer; Campbell; Forrester, 1985); moreover, the toxins of these bacteria induce biological effects also similar to those induced by the venom of *Loxosceles* (Bernheimer; Campbell; Forrester, 1985; Forrester; Barrett; Campbell, 1978; McNamara; Cuevas; Songer, 1995; Rees et al., 1984; Tambourgi et al., 1998, 2002, 2007).

*Corynebacterium pseudotuberculosis, Corynebacterium ulcerans* and *Arcanobacterium haemolyticum* are pathogens of pets and humans (McNAMARA et al., 1995).

*C. pseudotuberculosis* is a gram positive *Bacillus* widely distributed in animal populations, causing caseous lymphadenitis in sheep, goats and both, ulcerative inflammation of the wall of the lymphatic vessels and pectoral, abdominal and inguinal abscesses in horses (Soger et al., 1990; Huerta et al., 2013). Infections also occur in cattle and humans. These infections lead to reduced production and milk quality in cattle and goats and to a low yield of wool in sheep (Hoelzle et al., 2013). In the mechanism of pathogenesis of bacteria *C. pseudotuberculosis*, sphingomyelinase (PLD) has been shown as an essential determinant of virulence, which contributes to bacteria spreading from the initial site of infection to secondary host sites (Nairn et al., 1977). Knockout PLD strains have shown reduced virulence, emphasizing the importance of this toxin in the pathogenesis (Hodgson et al., 1992; McNamara et al., 1994).

*Arcanobacterium haemolyticum* are gram-positive bacteria responsible for many respiratory infections in healthy people. Most cases involve pharyngitis and/or tonsillitis, and approximately 50% are exsudative. Throat infections are often accompanied by cervical lymphadenopathy (GREEN et al., 1981; MACKENZIE et al., 1995). This bacterium produces a PLD which acts preferentially on sphingomyelin, generating ceramide-1-phosphate in the target membrane and being closely related to the PLD produced by *C. pseudotuberculosis* (Linder, 1997).

*Corynebacterium ulcerans* has its main reservoir in cattle herd, in which it induces mastitis, however, cases in human patients have been reported (DIAS et al., 2009). This bacterium can produce diphtheria toxin (DT) and/or PLD, and can cause infections in humans, mimicking the cutaneous and the classic respiratory diphtheria with pseudomembranas (Dewinter et al., 2005; Tiwari et al., 2008). Furthermore, the *C. ulcerans* strains that produce PLD, but not DT, also affect the lower respiratory tract and are capable of causing severe disease in humans, such as pneumonia (Mane-Guaraldi et al., 2008) and granulomatous nodules in lungs (Deseau et al., 1995).

Figure 17:
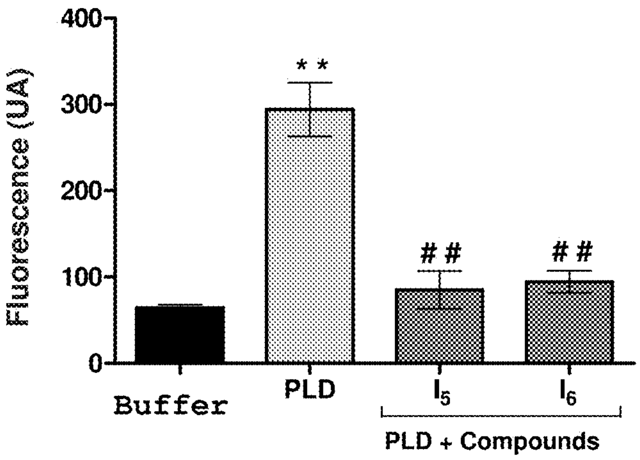
FIG. 17 shows the action of inhibitor compounds 5 and 6 on the substrate hydrolytic activity of PLD of *Corynebacterium pseudotuberculosis;*

Similarities in physical properties and activities of PLDs produced by *C. pseudotuberculosis, C. ulcerans* and *Arcanobacterium haemolyticum* suggest that this group of enzymes is important in the pathogenesis of diseases caused by these organisms. Thus, considering such similarities in PLD activities and clinical conditions induced by these bacteria and by *Loxosceles* toxins, it is important to test the compounds with activity on the *Loxosceles* SMases D on the PLD activity of some of these bacteria in order to possibly obtain compounds that help in the treatment of these diseases that affect farm animals and humans.

for this, 50 µg of PLD of *C. pseudotuberculosis* incubated with 40 µM of inhibitor compounds 5 and 6, and the residual hydrolytic activity on sphingomyelin were evaluated by fluorimetry. The results showed that the PLD activity of *C. pseudotuberculosis* was reduced about 70% by compound 5 and about 68% by compound 6 (FIG. 17).

Another class of phospholipases produced by bacteria and related to the virulence of the same are phospholipases C (PLC). Bacteria such as *Staphylococcus aureus, Bacillus cereus, Leptospira* and *Listeria*, among others, are some of the PLC producers.

*Bacillus cereus* is well known for its role as a mediator of foodborne diseases (Taylor & Gilbert, 1975; Gianella & Brasile, 1979; Stenfors et al., 2008; Bottone, 2010). This organism form spores and is widely distributed in dust, air and water, and therefore, it is ubiquitous in hospital environments, infecting clothings and intravenous catheters, thus providing an opportunity for infection in immunocompromised patients (Drobniewski, 1993). Generally, the infection caused by this organism leads to mild gastroenteritis, however, outbreaks of deadly food poisoning by *B. cereus* (Lund et al., 2000; DIERICK et al., 2005) and local and systemic infections out of the gastrointestinal tract (endophthalmitis, pneumonia and sepsis) in humans have been reported (Bottone, 2010).

*B. cereus* secrets several toxins that target cell membranes, including Bc-SMases. Evidences point out that, in *Listeria ivanovii,* PLC can act on the exit of the bacteria inside the phagocytic vacuoles, thus promoting the intracellular survival and spread of the pathogen (Gonzalez-Zorn et al., 1999). SMase derived from *Helicobacter pylori* directly contributes to the cytotoxicity on gastric cells (Tseng et al., 2004) and toxins with SMase activity are expressed by 91% of the *Staphylococcus aureus* strains of high toxicity (Collins et al., 2008).

Recent studies have shown that Bc-SMases lyse sheep red blood cells containing large amounts of sphingomyelin in the membrane (Oda et al., 2010), that these belong to the same group of SMases from *H. pylori* and *L. ivanovii* (Openshaw et al., 2005) and that the hydrolysis of sphingomyelin in the membrane of macrophages generates ceramide, which mitigates the fluidity of the membrane, leading to an unsuccessful phagocytosis. Therefore, PLC or Bc-SMase plays a key role in the bypass of the bacteria on immune mechanisms in macrophages (Oda et al., 2012).

*S. aureus* produces and secretes a large number of cell surface virulence factors that enable this organism to cause a variety of human diseases ranging from relatively mild eruptions and subcutaneous abscesses to severe septic shock and necrotizing pneumonia (Lowy, 1998; McCormick et al., 2001), moreover, *S. aureus* was also found in cases of bovine mastitis (Aarestrup et al., 1999). One of the exotoxins produced is a beta-toxin with mass about 35 kDa which seems to work like a SMase, being classified as a PLC (Huseby et al., 2007). This toxin causes lysis of red blood cells and other cells, such as lymphocytes and neutrophils (Marshall et al., 2000), being found in 72% of the cases of bovine mastitis, 11% in bacteria isolated from nostrils of healthy people and in 13% of cases of septic shock (Aarestrup et al., 1999). In general, studies suggest that this toxin can also contribute to immunomodulation of the host in the presence of other virulence factors (HUSEBY et al., 2007).

Figure 18:
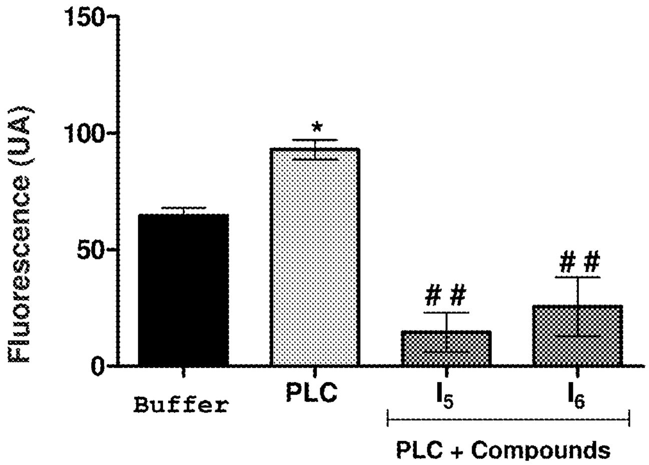
FIG. 18 shows the action of inhibitor compounds 5 and 6 on the hydrolytic activity on sphingomyelin substrate, of PLD of *Bacillus cereus.
Figure 19:
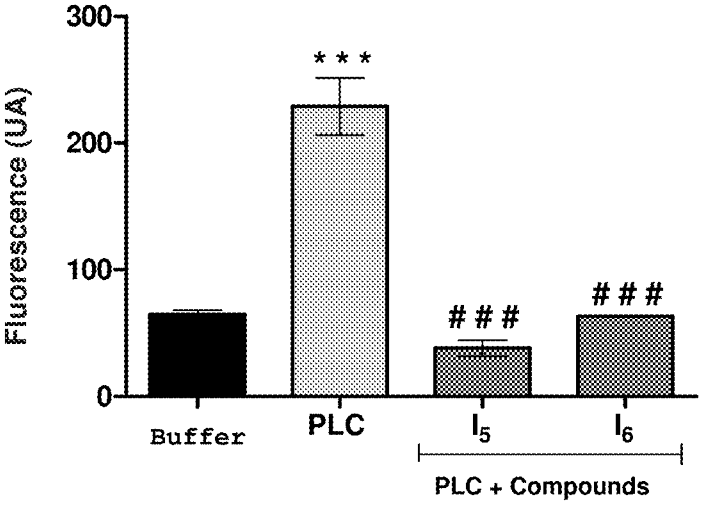
* and FIG. 19 shows the action of inhibitor compounds 5 and 6 on the hydrolytic activity on sphingomyelin substrate, of PLD of *Staphylococcus aureus.*

Thus, knowing the importance of PLCs in infections by some bacteria, compounds 5 and 6 (40 μM) were tested in face of the hydrolytic activity of SMases of *B. cereus* and *Stahylococcus aureus.* The results showed that the activities of SMases from both bacteria were efficiently reduced by incubation with compounds 5 and 6 (FIGS. 18 and 19).

Besides of the cited bacteria, other bacteria highly pathogenic to animals and to men, such as *Leptospira interrogans* (Kasarov & Addamiano, 1969; Nayaranavari et al., 2012), *Listeria ivanovii* (Gonzalez-Zorn et al., 1999), *Helicobacter pylori* (Tseng et al., 2004) and *Pseudomonas* sp (Sueyoshi et al., 2002), among others, also produce PLDs or PLCs, which usually are part of the virulence mechanisms. In addition to bacteria, parasites such as *Clonorchis sinensis* (Huang et al., 2013), ticks of the genus *Ixodes* (Alarcon-Chaidez et al., 2009), and fungi of the genus *Aspergillus* and *Coccidioides* (Fry et al., 2009) also produce such molecules.

Therefore, based on the results presented herein and on the similarity of the physical properties and biological activities between SMases of *Loxosceles* and of bacteria and other organisms, we propose here that the compounds 5 and 6, selected through molecular docking studies on the tertiary structure of SMase D I of *Loxosceles laeta,* can be used as tools to study the virulence mechanisms of these organisms, as well as a possible basis for the development of complementary therapeutic strategies for the control of diseases caused by these organisms.

Therefore, compounds 5 and 6 of the present invention can be used:

For preparing a medicine to act on the hydrolytic activity of recombinant toxin sphingomyelinase D (SMase D) and of the venom of brown recluse spider *Loxosceles laeta;*

For preparing a medicine to act on hemolysis reduction,

For preparing a medicine to inhibit skin lesion,

For preparing a medicine to inhibit dermonecrosis,

For preparing a medicine to inhibit mechanisms involved in the toxicity of SMases D in the development of loxoscelism;

For preparing a medicine to inhibit intracellular signaling pathways and the production of reactive oxygen species Besides of the fact that compounds 5 and 6 of the present invention act as inhibitors of sphingomyelinases D of the venom of spiders of the genus *Loxosceles,* they can also act as a complimentary therapeutic drug for accidents and possibly as compounds for controlling the effects of bacterial sphingomyelinases (*Coryneumbacterium pseudotuberculosis, Arcanobacterium haemoliticum, Bacillus cereus*) and some arthropods (spiders, scorpions and ticks).

In a second aspect, this invention relates to a pharmaceutical composition for treating loxoscelism, hemolysis reduction, inhibition of cutaneous lesion, inhibition of dermonecrosis, inhibition of intracellular signaling pathways and production of reactive oxygen species, which comprises a benzenesulfonamide compound and a pharmaceutically acceptable vehicle. The benzenesulfonamide compound preferably being the compound 4-bromo-N-[(E)-(2-methyl-1H-indol-3-yl)methyleneamine]benzenesulfonamide.

A third aspect of this invention relates to a pharmaceutical composition for treating loxoscelism, hemolysis reduction, inhibition of cutaneous lesion, inhibition of dermonecrosis, inhibition of intracellular signaling pathways and production of reactive oxygen species, which comprises a benzenesulphonate compound and a pharmaceutically acceptable vehicle. The benzenesulphonate compound preferably being compound 4-methyl-3-oxo-2-(3-pyridylmethylene)benzo[3,4-b]furan-6-yl-4-chlorobenzenesulfonate.

It is understood, by "pharmaceutically acceptable vehicle" any acceptable vehicle, excipient or diluent in the pharmaceutical field.

Thus, although only some details of the present invention have been shown, it will be understood that several omissions, substitutions and changes to classes of benzenesulfonamide and benzenesuphonate compounds can be made by a person skilled in the art, without departing from the spirit and scope of this invention.

It is expressly provided that all combinations of the elements that perform the same function substantially the same way to achieve the same results are within the scope of the invention. Substitution of elements in an embodiment described to another are also fully comprised and contemplated.

It should be also understood that the drawings are not necessarily in scale, and are only conceptual in nature. The intention is, therefore, to be limited, as indicated by the scope of the attached claims.

REFERENCES

Aarestrup, F. M.; Larsen, H. D.; Eriksen, N. H.; Elsberg, C. S.; Jensen, N. E. Frequency of α and β-haemolysin in

*Staphylococcus aureus* of bovine and human origin. A comparison between pheno- and genotype and variation in phenotypic expression. APMIS, 107: 425-430, 1999.

Alarcon-Chaidez, F. J.; Boppana, V. D.; Hagymasi, A. T.; Adler, A. J.; Wikel, S. K. A novel sphingomyelinase-like enzyme in *Ixodes scapularis* tick saliva drives host CD4 T cells to express IL-4. Parasite Immunol, 31: 210-219, 2009.

Bernheimer, A. W.; Campbell, B. J.; Forrester, L. J. Comparative toxinology of *Loxosceles reclusa* and *Corynebacterium pseudotuberculosis*. Science, v. 228, p. 590, 1985.

Bottone, E. J. *Bacillus cereus,* a volatile human pathogen. Clin Microbiol Rev, 23: 382-398, 2010.

Collins, J.; Buckling, A.; Massey, R. C. Identification of factors contributing to T-cell toxicity of *Staphylococcus aureus* clinical isolates. J Clin Microbiol, 46: 2112-2114, 2008.

Desseau, R. B.; Brandt-Christensen, M.; Jensen, O. J.; Tonnesen, P. Pulmonary nodules due to *Corynebacterium ulcerans*. Eur Respir, 8: 651-653, 1995.

Dewinter, L. M.; Bernard, K. A.; Romney, M. G.; Human clinical isolates of *Corynebacterium diphtheriae* and *Corynebacterium ulcerans* collected in Canada from 1999 to 2003 but not fitting reporting criteria for cases of diphtheria. J Clin Microbiol, 43: 3447-3449, 2005.

Dias, A. A. S. O; Silva Junior, F. C.; Pereira, G. A.; Souza, M. C.; Camello, T. C. F.; Damasceno, J. A. L. D.; Pacheco, L. G. C.; Miyoshi, A.; Azevedo, V. A.; Hirata Junior, R.;. Bôas, M. H. S. V.; Mattos-Guaraldi, A. L. *Corynebacterium ulcerans* isolated from an asymptomatic dog kept in an animal shelter in the metropolitan area of Rio de Janeiro, Brazil. Vector-Borne and Zoonotic diseases, 10(8), 2010.

Dierick, K.; Van Coillie, E.; Swiecicka, I.; Meyfroidt, G.; Devlieger, H.; Meulemans, A.; Hoedemaekers, G.; Fourie, L.; Heyndrickx, M.; Mahillon, J. Fatal family outbreak of *Bacillus cereus*-associated food poisoning. J Clin Microbiol, 43: 4277-4279, 2005.

Drobniewski, F. A. *Bacillus cereus* and related species. Clin Microbiol Rev, 6(4): 324-338, 1993.

Forrester, L. J.; Barret, J. T.; Campbell, B. Red blood cells lysis induced by the venom of the brown spider: the role of sphingomielinase D. J. Arch. Biochem. Biophys, 187: 355-365, 1978.

Fry, B. G.; Roelants, K.; Champagne, D. E.; Scheib, H.; Tyndall, J. D. A.; King, G. F.; Nevalainen, T. J.; Norman, J. A.; Lewis, R. J.; Norton, R. S.; Renjifo, C.; de la Vega, R. C. The toxicogenomic multiverse: convergent recruitment of proteins into animal venoms. Annu Rev Genomics Hum Genet 10: 483-511, 2009.

Giannella, R. A. & Brasile, L. A hospital food-borne outbreak of diarrhea caused by *Bacillus cereus:* clinical, epidemiologic, and microbiologic studies. J Infect Dis, 139: 366-370, 1979.

Gonzalez-Zorn, B.; Dominguez-Bernal, G.; Suarez, M.; Ripio, M. T.; Vega, Y.; Novella, S.; Vazquez-Boland, J. A. The smcL gene of *Listeria ivanovii* encodes sphingomyelinase C that mediates bacterial escape from the phagocytic vacuole, Mol. Microbiol, 33: 510-523, 1999.

Green, S. L.; LaPeter, K. S. Pseudodiphtheritic membranous pharyngitis caused by *Corynebacterium hemolyticum.* JAMA, 2330-2331, 1981.

Hodgson, A. L. M.; Krywult, J.; Corner, L. A.; Rothel, J. S.; Radford, A. J. Rational attenuation of *Corynebacterium pseudotuberculosis:* potential cheesy gland vaccine and live delivery vehicle. Infect. Immun., 60: 2900-2905, 1992.

Hoelzle, L. E.; Scherrer, T.; Muntwyler, J.; Wittenbrink, M. M.; Philipp, W.; Hoelzle, K. Differences in the antigen structures of *Corynebacterium pseudotuberculosis* and the induced humoral immune response in sheep and goats. Veterinary Microbiology, 164: 359-365, 2013.

Huang, Y.; Zheng, Y.; Li, Y.; Yang, M.; Li, T.; Zeng, S.; Yu, X.; Huang, H.; Hu, X. Expression, immunolocalization, and serological reactivity of a novel sphingomyelin phosphodiesterase-like protein, an excretory/secretory antigen from *Clonorchis sinensis,* Parasitol Res, 112: 2197-2206, 2013.

Huerta, B.; Gómez-Gascon, L.; Vela, A. I.; Fernández-Garayzábal, J. F.; Casamayor, A.; Tarradas, C.; Maldonado, A. Comparison of two biochemical methods for identifying *Corynebacterium pseudotuberculosis* isolated from sheep and goats. The Veterinary Journal, 196, 552-554, 2013.

Huseby, M.; Shi, K.; Kent Brown, C.; Digre, J.; Mengistu, F.; Seo, K. S.; Bohach, G. A; Schlievert, P. M.; Ohlendorf, D. H.; Earhart, C. A. Structure and Biological Activities of Beta Toxin from *Staphylococcus aureus.* Journal of Bacteriology, 189(23): 8719-8726, 2007.

Kasarov, L. B. & Addamiano, L. Degradation of the phospholipids of the serum lipoproteins by leptospirae. J Med Microbiol, 2: 243-248, 1969.

Linder, R. *Rhodococcus equi* and *Arcanobacterium haemolyticum:* Two "Coryneform" Bacteria Increasingly Recognized as Agents of Human Infection. Emerging Infectious Diseases, 3(2), 1997.

Lowy, F. D. *Staphylococcus aureus* infections. N. Engl. J. Med. 339: 520-532, 1998.

Lund, T.; De Buyser, M. L.; Granum, P. E. A new cytotoxin from *Bacillus cereus* that may cause necrotic enteritis. Mol Microbiol 38: 254-261, 2000.

Mackenzie, A.; Fuite, L. A.; Chan, F. T. H.; King, J.; Allen, A.; MacDonald, N.; Diaz-Mitoma, F. Incidence and pathogenicity of *Arcanobacterium haemolyticum* during a 2-year study in Ottawa. Clin Infect Dis, 21: 177-181, 1995.

Marshall, M. J.; Bohach, G. A.; Boehm, D. F. Characterization of *Staphylococcus aureus* beta-toxin induced leukotoxicity. J. Nat. Toxins, 9: 125-138, 2000.

Mattos-Guaraldi, A. L.; Sampaio, J. L. M.; Santos, C. S.; Pimenta, F. P.; Pereira, G. A.; Pacheco, L. G. C.; Miyoshi, A.; Azevedo, V.; Moreira, L.O,; Gutierrez, F. L.; Costa, J. L. F.; Costa-Filho, R.; Damasco, P. V.; Camello, T. C. F.; Hirata Jr, R. First detection of *Corynebacterium ulcerans* producing diphtheria-like toxin in human with pulmonary infection in Rio De Janeiro metropolitan area, Brazil. Mem Inst Oswaldo Cruz, 103: 396-400, 2008.

McCormick, J. K.; Yarwood, J. M.; Schlievert, P. M. Toxic shock syndrome and bacterial superantigens: an update. Annu. Rev. Microbiol., 55:77-104, 2001.

McNamara, P. J.; Bradley, G. A; Songer, J. G. Targeted mutagenesis of the phospholipase D gene results in decreased virulence of *Corynebacterium pseudotuberculosis.* Mol. Microbiol., 12, 1994.

McNamara, P. J.; Cuevas, W. A.; Songer, J. G. Toxic phospholipases D of *Corynebacterium pseudotuberculosis, C. ulcerans* and *Arcanobacterium haemolyticum:* cloning and sequence homology. Gene, 156: 113-118, 1995.

Nairn, M. E.; Robertson, J. P; McQuade, N. C. The control of caseous lymphadenitis in sheep by vaccination. Proc. Annu. Meet. Aust. Vet. Ass., 54: 159-161, 1977.

Narayanavari, S. A.; Sritharan, M.; Haake, D. A.; Matsunaga, J. Multiple leptospiral sphingomyelinases (or are there?) Microbiology, 158, 1137-1146, 2012.

Oda, M.; Takahashi, M.; Matsuno, T. Uoo, K.; Nagahama, M.; Sakurai, J. Hemolysis induced by *Bacillus cereus* sphingomyelinase. Biochimica et Biophysica Acta, 1798: 1073-1080, 2010.

Oda, M.; Hashimoto, M.; Takahashi, M.; Ohmae, Y.; Seike, S.; Kato, R.; Fujita, A.; Tsuge, H.; Nagahama, M.; Ochi, S.; Sasahara, T.; Hayashi, S.; Hirai, Y.; Sakurai, J. Role of sphingomyelinase in infectious diseases caused by *Bacillus cereus.* PLoS ONE, 7(6): e38054, 2012.

Openshaw, A. E..; Race, P. R.; Monzo, H. J.; Vazquez-Boland, J. A.; Banfield, M. J. Crystal structure of SmcL, a bacterial neutral sphingomyelinase C from *Listeria.* J Biol Chem, 280: 35011-35017, 2005.

Rees, R. S.; Nanney, L. B.; Yates, R. A.; King, L. J. Interaction of brown recluse spider venom on cell membranes: the inciting mechanism? J. Invest. Dermatol., 83: 270-275, 1984.

Songer, J. G.; Libby, S. J.; Iandolo, J. J.; Cuevas, W. A. Cloning and Expression of the Phospholipase D Gene from *Corynebacterium pseudotuberculosis* in *Escherichia coli.* Infection and Immunity, 58(1): 131-136, 1990.

Stenfors Arnesen, L. P.; Fagerlund, A.; Granum, P. E. From soil to gut: *Bacillus cereus* and its food poisoning toxins. FEMS Microbiol Rev, 32: 579-606, 2008.

Sueyoshi, N.; Kita, K.; Okino, N.; Sakaguchi, K.; Nakamura, T.; Ito, M. Molecular Cloning and Expression of $Mn^2$+ Dependent Sphingomyelinase/Hemolysin of an Aquatic Bacterium, *Pseudomonas* sp. Strain TK4. Journal of Bacteriology, 184(2): 540-546, 2002.

Tambourgi, D. V.; Magnoli, F. C.; van den Berg, C. W.; Morgan, B. P.; Araujo, P. S.; Alves, E. W.; Dias da Silva, W. Sphingomyelinases in the venom of the spider *Loxosceles intermedia* are responsible for both dermonecrosis and complement-dependent hemolysis. Biochem. Biophys. Res. Commun., 251: 366-373, 1998.

Tambourgi, D. V.; Silva, M. S.; Billington, S. J.; Gonçalves de Andrade, R. M.; Magnoli, F. C.; Songer, J. G.; van den Berg, C. W. Mechanism of induction of complement susceptibility of erythrocytes by spider and bacterial sphingomyelinases. Immunol., 107: 93-101, 2002.

Tambourgi, D. V.; Fernandes-Pedrosa, F. M.; Gonçalves DE Andrade, R. M.; Billington, S. J.; Griffiths, M.; van den Berg, C. W. Sphingomyelinases D induce direct association of Clq to the erythrocyte membrane causing complemente mediated autologous haemolysis. Mol. Immunol., 44: 576-582, 2007.

Taylor, A. J. & Gilbert, R. J. *Bacillus cereus* food poisoning: a provisional serotyping scheme. J Med Microbiol., 8: 543-550, 1975.

Tiwari, T. S.; Golaz, A.; Yu, D. T.; Ehresmann, K. R.; Jones, T. F.; Hill, H. E.; Cassiday, P. K.; Pawloski, L. C.; Moran, J. S.; Popovic, T.; Wharton, M. Investigations of 2 cases of diphtheria-like illness due to toxigenic *Corynebacterium ulcerans.* Clin Infect Dis., 46: 395-401, 2008.

Tseng, H. J.; Chan, C. C.; Chan, E. C. Sphingomyelinase of *Helicobacter pylori* induced cytotoxicity in AGS gastric epithelial cells via activation of JNK kinase. Biochem Biophys Res Commun., 314: 513-518, 2004.

Van den Bosch, H. Intracellular phospholipases A. Biochem. Biophys. Acta, 604: 191-246, 1980.

Van Meeteren, L. A.; Frederiks, F.; Giepmans, B. N.; Pedrosa, M. F.; Billington, S. J.; Jost, B. H.; Tambourgi, D. V.; Moolenaar, W. H. Spider and bacterial sphingomyelinases D target cellular lysophosphatidic acid receptors by hydrolyzing lysophosphatidylcholine. J. Biol. Chem., 279: 10833-10836, 2004.

The invention claimed is:

1. A pharmaceutical composition comprising (1) a compound selected from the group consisting of 4-bromo-N-[(E)-(2-methyl-1H-indol-3-yl)methylene amino]benzenesulfonamide and 4-methyl-3-oxo-2-(3-pyridylmethylene) benzo[3,4-b]furan-6-yl-4-chlorobenzenesulfonate and (2) a pharmaceutically acceptable vehicle.

2. The pharmaceutical composition, of claim 1, wherein the compound is 4-bromo-N-[(E)-(2-methyl-1H-indol-3-yl) methylene amino]benzenesulfonamide.

3. The pharmaceutical composition, of claim 1, wherein the compound is 4-methyl-3-oxo-2-(3-pyridylmethylene) benzo[3,4-b]furan-6-yl-4-chlorobenzenesulfonate.

4. The pharmaceutical composition of claim 1, which inhibits the toxicity of D sphingomyelinases in the venom of *Loxosceles* spiders.

5. The pharmaceutical composition of claim 4, wherein the compound is the benzenesulfonamide compound and wherein the benzenesulfonamide compound is 4-bromo-N-[(E)-(2-methyl-1H-indol-3-yl)methyleneamino]benzenosulfonamide.

6. The pharmaceutical composition of claim 4, wherein the compound is the benzenesulphonate compound, wherein the benzenesulphonate compound is 4-methyl-3-oxo-2-(3-pyridylmethylene)benzo[3,4-b]furan-6-yl-4-chlorobenzenesulfonate.

7. The pharmaceutical composition of claim 4, wherein the compound acts on the hydrolytic activity of recombinant toxin sphingomyelinase D (D SMase) and of venom of brown recluse spider.

8. The pharmaceutical composition of claim 4, wherein the compound controls the development of cutaneous and systemic loxoscelism.

9. The pharmaceutical composition of claim 5, wherein the 4-bromo-N-[(E)-(2-methyl-1H-indol-3-yl)methylene amino]benzenesulfonamide:

(1) inhibits by 45.7% the activity of recombinant toxin D SMase on a sphingomyelinase (SM) substrate, (2) inhibits by 53% the activity of the venom of *L. laeta* on SM substrate, (3) reduces by 38.6% the activity of recombinant toxin D SMase in relation to lysophosphatidylcholine (LPC) substrate, (4) reduces by 44.4% the venom activity in relation to LPC substrate, (5) has an $IC_{50}$ value of 45.4±1.2 μM, based on action of the compound on the activity of recombinant toxin on SM substrate, (6) reduces by 92.6% the removal of glycophorins from the surface of red blood cells, (7) reduces by 96.8% the removal of glycophorin C from the surface of red blood cells, (8) increases from 20.23% to 55.75% the viability of cells treated with the recombinant toxin D SMase, (9) increases from 36.7% to 45.9% the viability of cells treated with the venom,

(10) reduces by 81% secretion of extracellular matrix metalloproteinases 2 (MMP-2) in keratinocytes treated with recombinant toxin D SMase,

(11) completely inhibits secretion of extracellular matrix metalloproteinases 9 (MMP-9) in keratinocytes treated with recombinant toxin D SMase,

(12) reduces disorganization of dermis collagen fibers, bleeding, inflammatory infiltrate, and injury to adjacent muscle layer in skin contacted with venom,

(13) inhibits by 70.7% superoxide production by keratinocytes treated with recombinant toxin D SMase,

(14) reverses by 27.7% the removal of TNF receptor from the surface of keratinocytes treated with recombinant toxin D SMase,

(15) reverses by 73.9% the production of TNF-α in keratinocytes treated with recombinant toxin D SMase,

(16) reduces by 88.3% the production of TGF-β1 in keratinocytes treated with recombinant toxin D SMase, or

(17) reduces by 65.8% phosphorylated ERK1/2 in keratinocytes treated with recombinant toxin D SMase.

10. The pharmaceutical composition of claim 6, wherein the 4-bromo-N-[(E)-(2-methyl-1H-indol-3-yl)methylene amino]benzenesulfonamide:

(1) inhibits by 51% the activity of recombinant toxin D SMase on SM substrate, (2) inhibits by 22.7% the activity of the venom of *L. laeta* on SM substrate, (3) reduces by 34% the activity of recombinant toxin D SMase in relation to LPC substrate, (4) reduces by 16% the activity of the venom in relation to substrate LPC, (5) has an $IC_{50}$ value is 63.4±1.1 μM, based on the action of the compound on the activity of recombinant toxin on SM substrate, (6) reduces by 88.2% the removal of glycophorins from the surface of red blood cells, (7) reduces by 84% the removal of glycophorin C from the surface of red blood cells, (8) increases from 20.23% to 53.55% the viability of cells treated with recombinant toxin D SMase, (9) increases from 36.7 to 59.26% the viability of cells treated with the venom,

(10) reduces by 98.4% the secretion of extracellular MMP-2 in keratinocytes treated with recombinant toxin D SMase,

(11) completely inhibits the secretion of extracellular MMP-9 in keratinocytes treated with recombinant toxin D SMase,

(12) reduces disorganization of dermis collagen fibers, bleeding, inflammatory infiltrate, and injury to adjacent muscle layer in skin contacted with venom,

(13) inhibits by 92.7% superoxide production by keratinocytes treated with recombinant toxin D SMase,

(14) reverses by 61.1% the production of TNF-α from the surface of keratinocytes treated with recombinant toxin D SMase,

(15) reduces by 89.2% the production of TGF-β1 from the surface of keratinocytes treated with recombinant toxin D SMase,

(16) reduces by 80.2% phosphorylated ERK1/2 in keratinocytes treated with recombinant toxin D SMase.

11. The pharmaceutical composition of claim 4, which controls the effects of sphingomyelinases from bacteria and from arthropods, wherein the arthropods are selected from the group consisting of (spiders, scorpions and ticks).

12. The pharmaceutical composition of claim 11, wherein the sphingomyelinases are from bacteria selected from the group consisting of *Coryneumbacterium pseudotuberculosis, Arcanobacterium haemoliticum*, and *Bacillus cereus.*

* * * * *